(12) United States Patent
Baker et al.

(10) Patent No.: US 8,068,258 B2
(45) Date of Patent: Nov. 29, 2011

(54) CALIBRATION OF ELECTRO-OPTICAL INSTRUMENTATION WITHIN PRINTING DEVICES

(75) Inventors: Douglas V. Baker, Middleville, MI (US); John Calow, Plainwell, MI (US)

(73) Assignee: X-Rite, Inc., Grand Rapids, MI (US)

( * ) Notice: Subject to any disclaimer, the term of this patent is extended or adjusted under 35 U.S.C. 154(b) by 934 days.

(21) Appl. No.: 11/788,929

(22) Filed: Apr. 23, 2007

(65) Prior Publication Data

US 2008/0013128 A1    Jan. 17, 2008

Related U.S. Application Data

(60) Provisional application No. 60/794,606, filed on Apr. 24, 2006.

(51) Int. Cl.
*H04N 1/21* (2006.01)

(52) U.S. Cl. ......................................... 358/3.24; 347/19

(58) Field of Classification Search .................. 358/3.26; 347/19
See application file for complete search history.

(56) References Cited

U.S. PATENT DOCUMENTS

| | | | |
|---|---|---|---|
| 4,003,660 A | 1/1977 | Christie, Jr. et al. | |
| 6,832,824 B1 | 12/2004 | Baker et al. | |
| 7,259,857 B2 * | 8/2007 | Butterfield et al. | 356/444 |
| 2004/0085385 A1 * | 5/2004 | Arquilevich et al. | 347/19 |
| 2006/0044367 A1 * | 3/2006 | Campillo et al. | 347/85 |
| 2006/0146321 A1 * | 7/2006 | Sezginer et al. | 356/241.1 |

FOREIGN PATENT DOCUMENTS

| | | |
|---|---|---|
| GB | 2 380 451 | 4/2003 |
| JP | 6-117996 | 4/1994 |

OTHER PUBLICATIONS

European Search Report, Aug. 9, 2007.

* cited by examiner

*Primary Examiner* — Benny Tieu
*Assistant Examiner* — Qian Yang
(74) *Attorney, Agent, or Firm* — McCarter & English, LLP

(57) ABSTRACT

Systems and methods are disclosed for positioning or storing an electro-optical instrument (e.g., spectrophotometer) within a printing device to facilitate calibration or maintenance of the instrument. In various embodiments, the electro-optical instrument may be pivoted or moved to an inclined position to facilitate calibration of the instrument relative to one or more calibration references. The electro-optical instrument may also be moved or inclined along a travel path in the printing device to a position or positions adjacent to various calibration references.

37 Claims, 10 Drawing Sheets

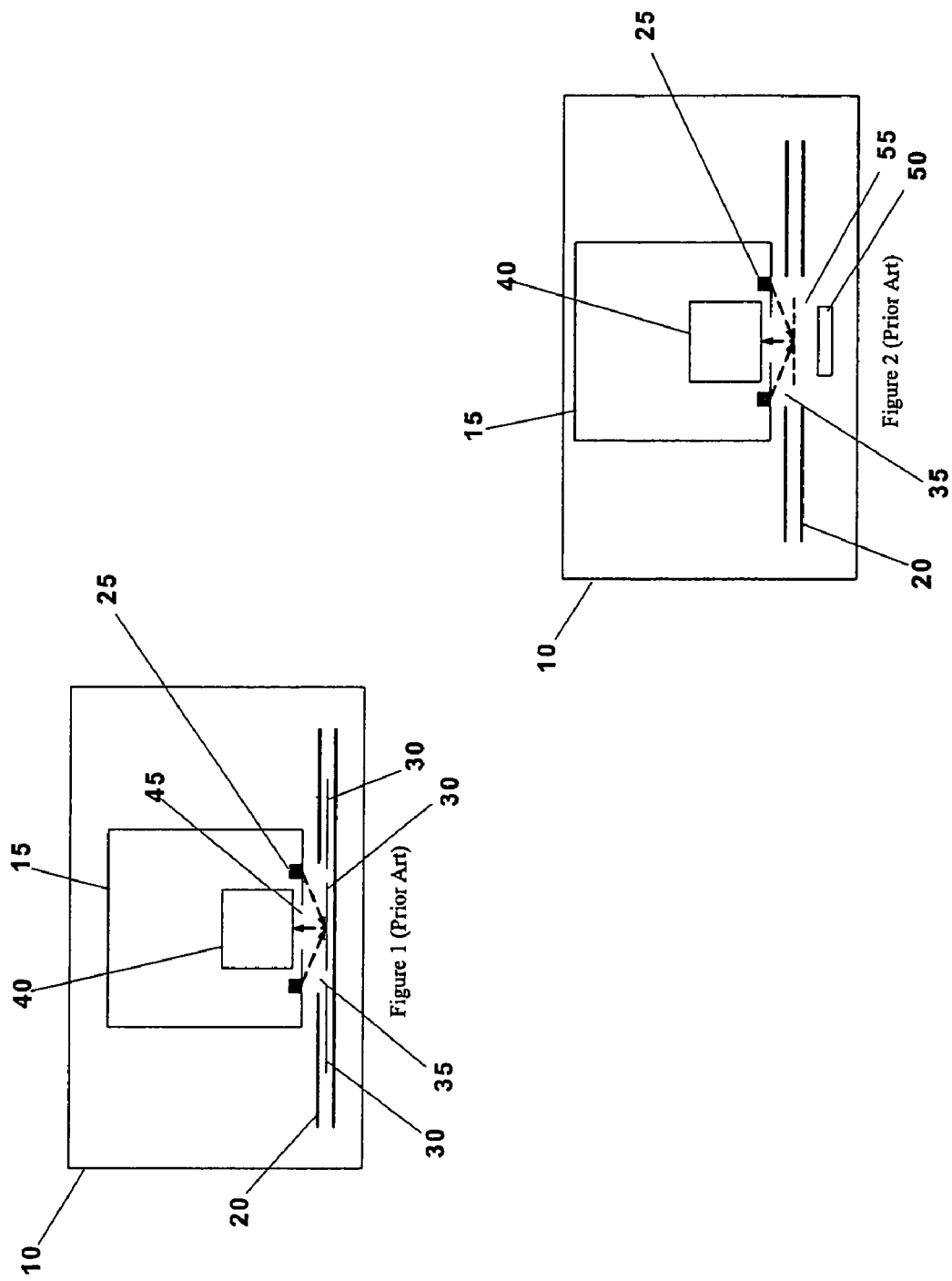

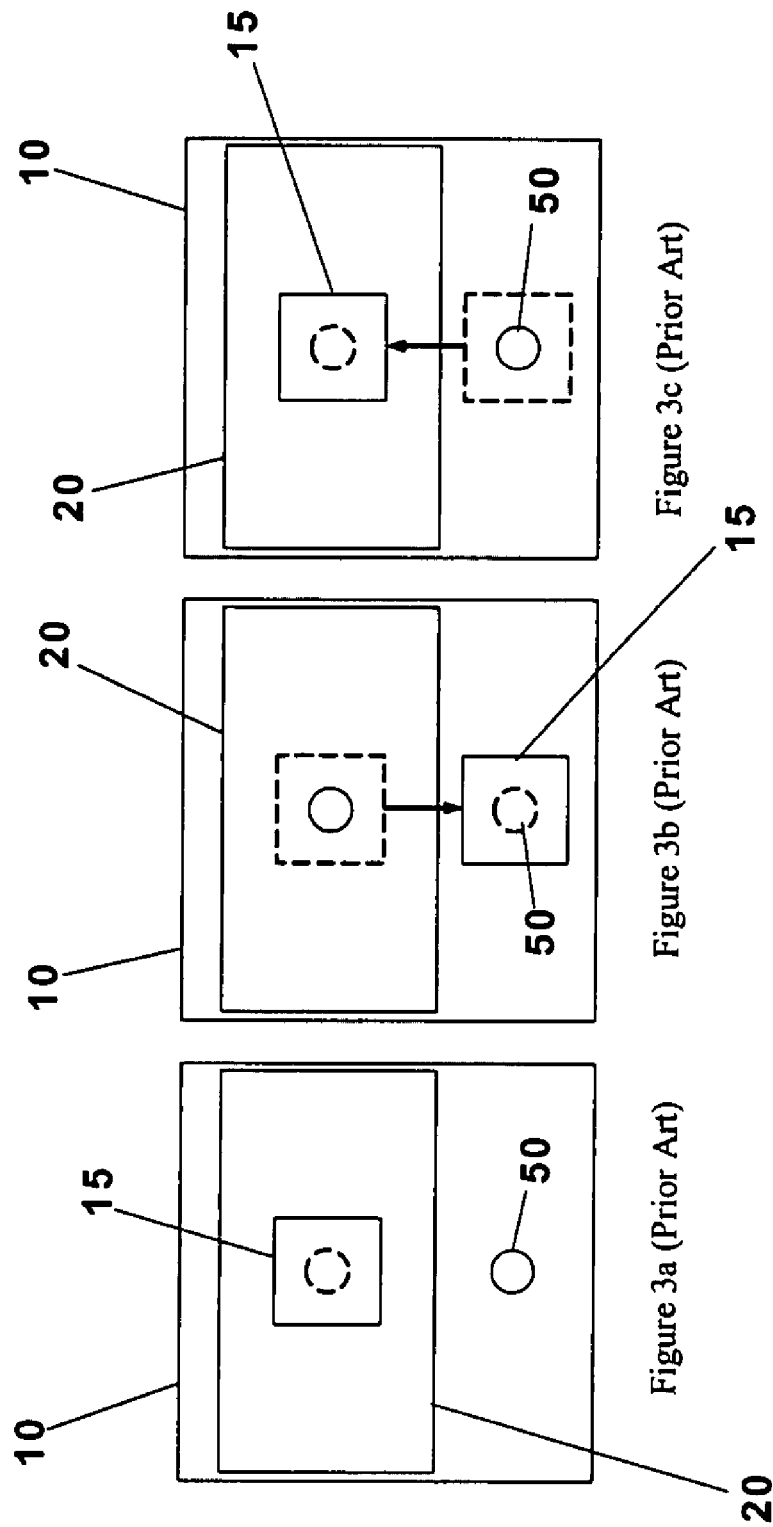

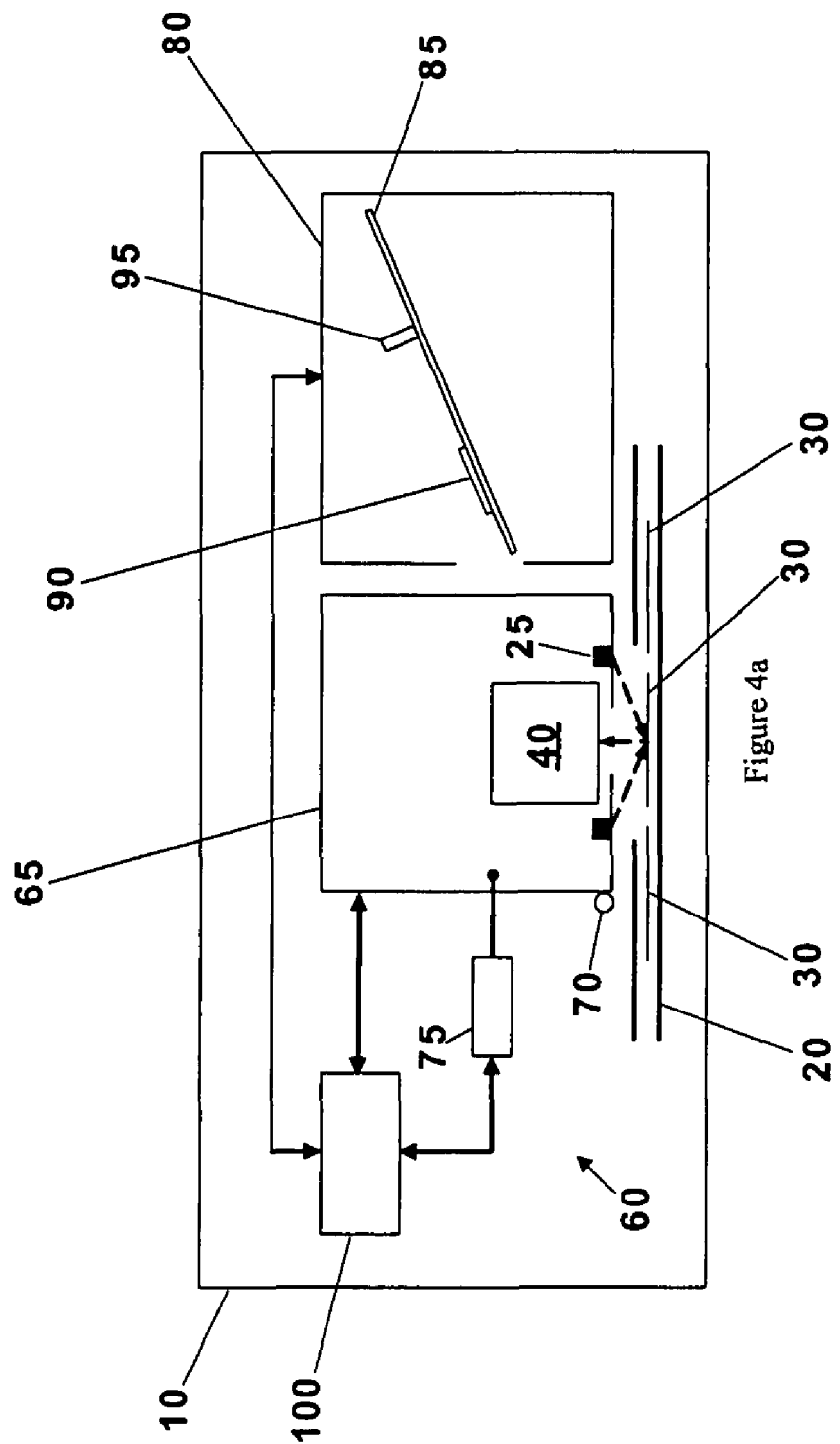

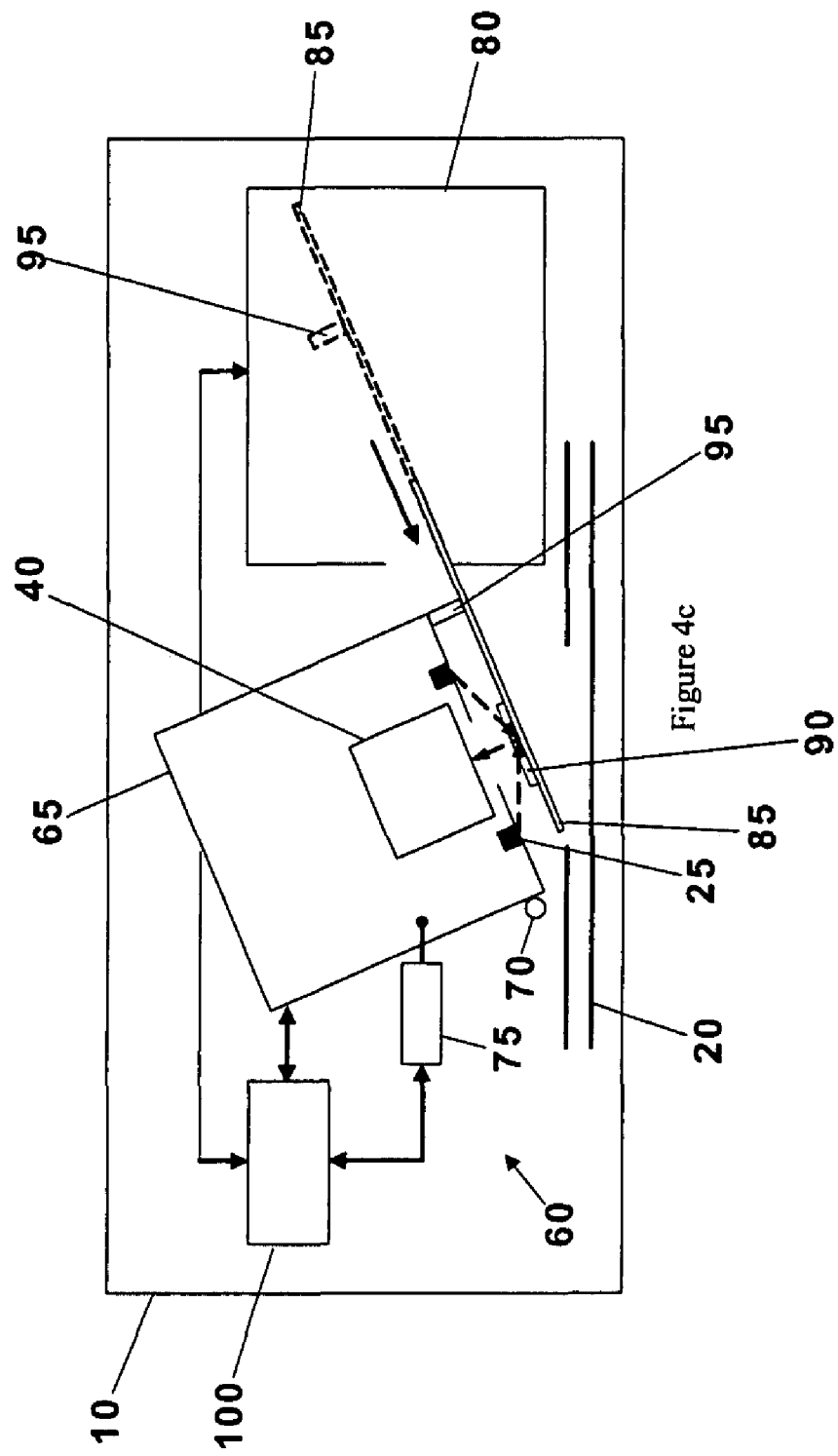

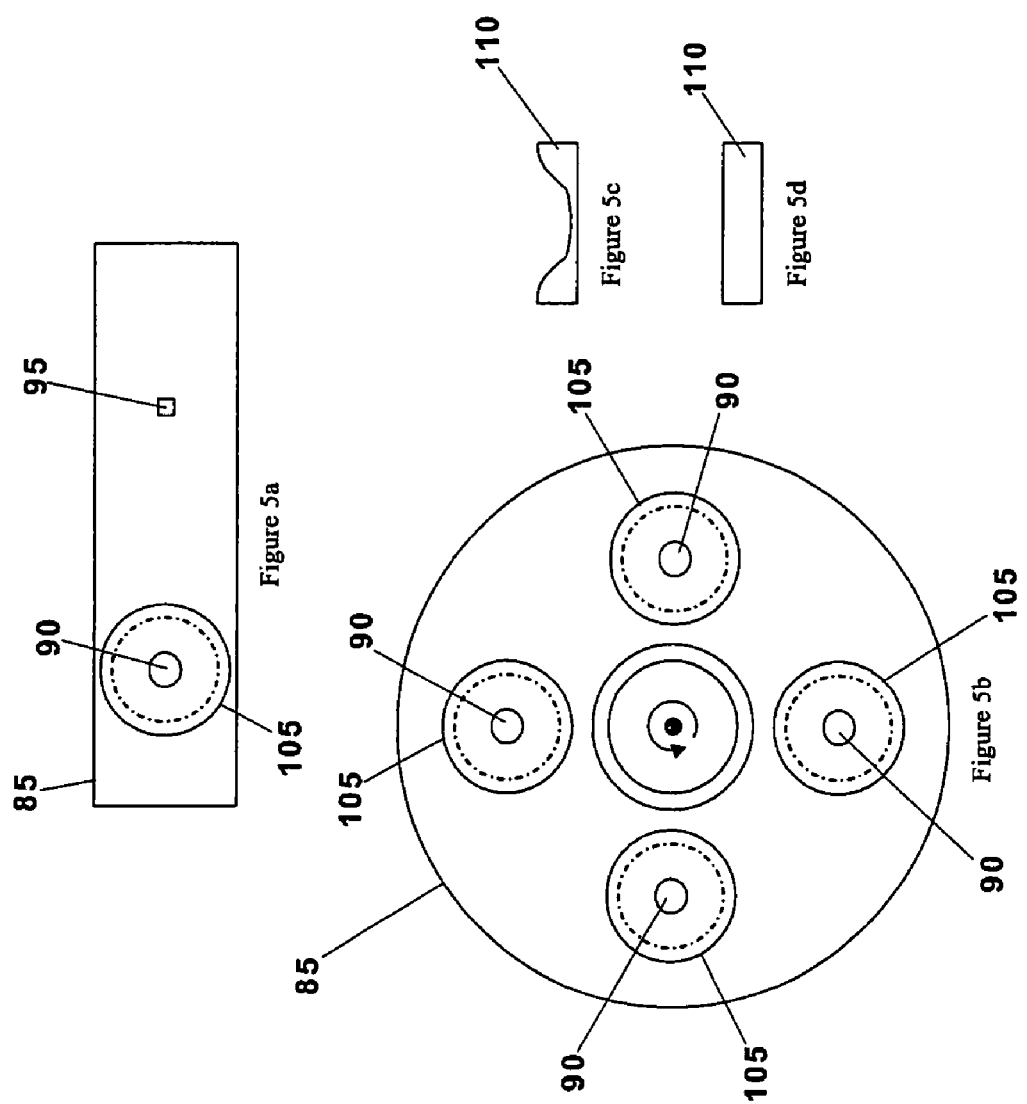

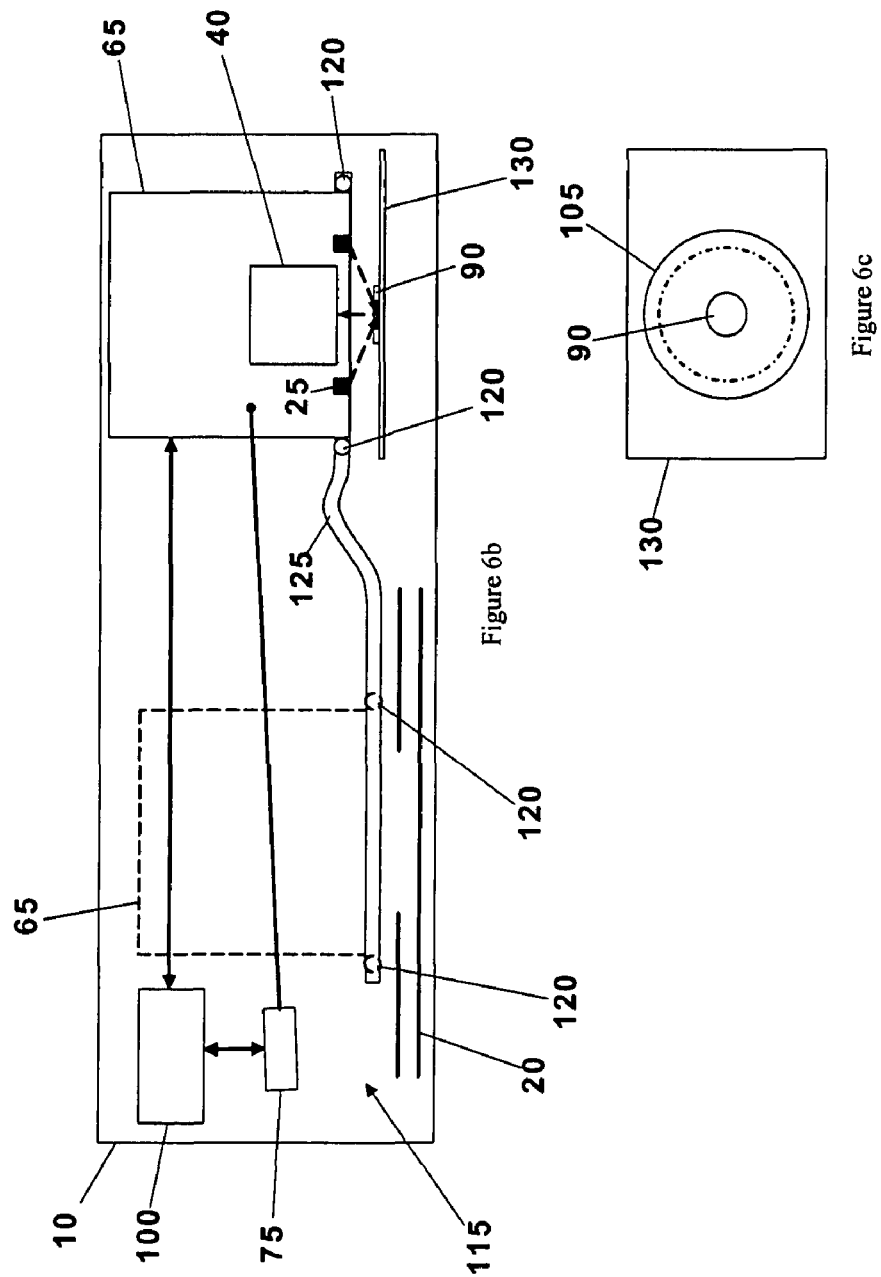

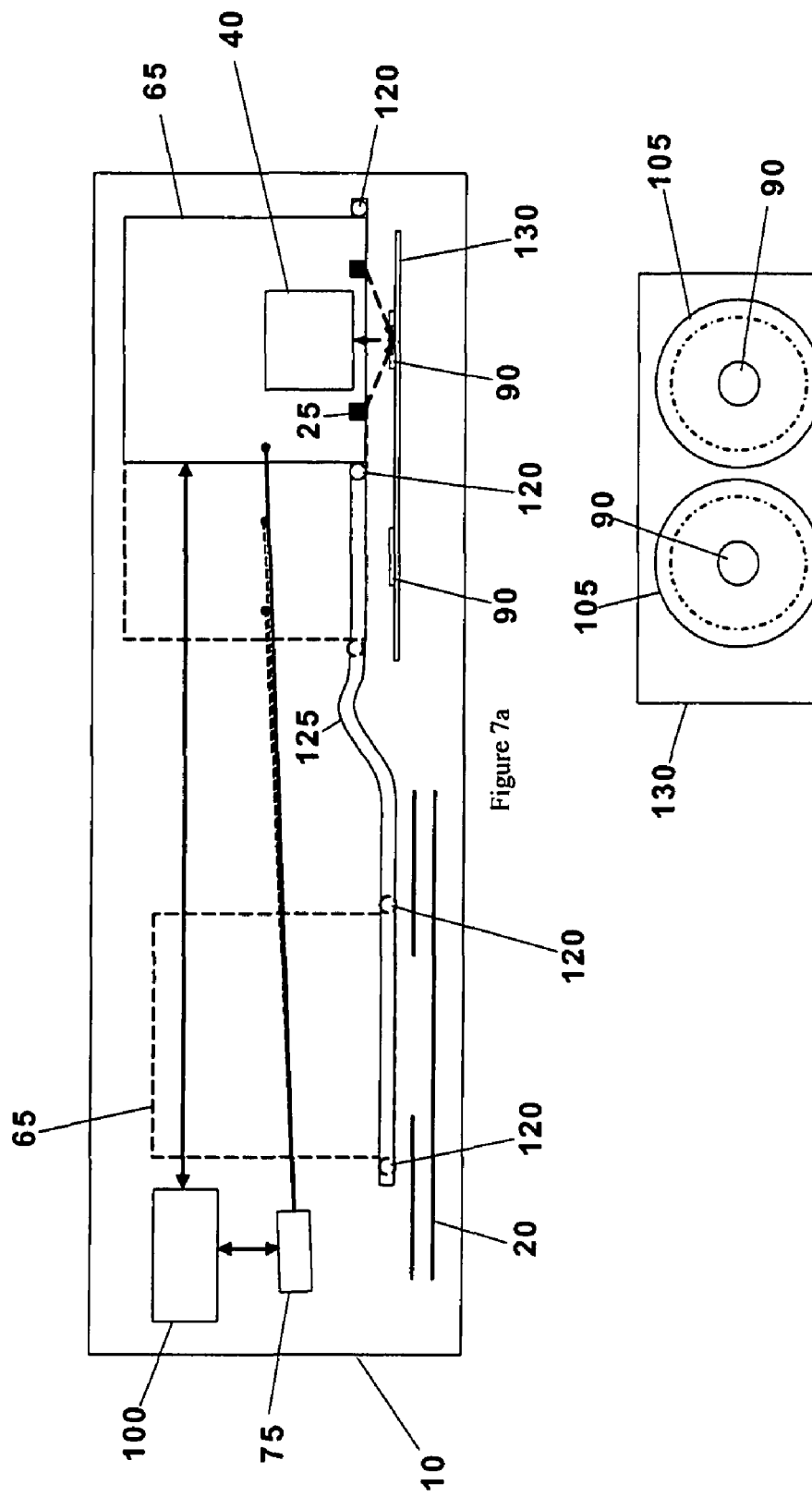

CALIBRATION OF ELECTRO-OPTICAL INSTRUMENTATION WITHIN PRINTING DEVICES

CROSS REFERENCE TO RELATED APPLICATION/PRIORITY CLAIM

The present application claims the benefit of U.S. Provisional Patent Application Ser. No. 60/794,606, filed on Apr. 24, 2006, the entirety of which is hereby incorporated by reference.

TECHNICAL FIELD OF THE INVENTION

This application is directed generally and in various embodiments to calibration, maintenance, and storage of electro-optical instrumentation, and more particularly, to automatic calibration and storage of electro-optical instrumentation within printing devices.

BACKGROUND

Digital printing presses and other digital printing devices (hereinafter "printing devices") may incorporate an electro-optical instrument, typically a reflection spectrophotometer, for automatically controlling print attributes. FIG. 1 illustrates a conventional arrangement of a reflection spectrophotometer 15 within a printing device 10. As shown, the spectrophotometer 15 may be oriented above a media guide 20 and include an illumination source 25 (e.g., an LED or lamp) for illuminating print media 30 (e.g., paper) via a first guide aperture 35 as the media 30 is passed through the guide 20. Although depicted as a slotted guide, the guide 20 may alternatively be a roller or other device for suitably directing the media 30. Light reflected from the media 30 is received by a sensor module 40 within the spectrophotometer 15 via an aperture 45. Although not shown for the sake of clarity, the sensor module 40 may include optics (e.g., lens, mirrors, etc.), light detectors (e.g., CCD sensors), and various electronics configured for processing the reflected light and generating spectral data therefrom. The spectral data may be communicated to a print engine (not shown) within the printing device 10 and used, for example, to control colors printed by the printing device 10 in accordance with a color desired standard. In order to ensure that the spectral data accurately represents the color characteristics of the media 30, the orientation of the spectrophotometer 15 is required to be such that its "read plane" (i.e., a plane parallel to the illuminating/detecting face of the spectrophotometer 15 corresponding to optimal illumination and light detection) precisely coincides with the upper surfaces of the media 30. Typically, the surfaces of the media 30 must be within several thousandths of an inch of a known read plane or at a known offset in order to obtain suitably accurate spectral data. Repeatability of such tolerances may be maintained, for example, by providing a reference surface (not shown) that contacts a portion of the illuminating/detecting face of the spectrophotometer 15 or reference features.

It is necessary to periodically calibrate the spectrophotometer 15 using a calibration reference. Typically, the calibration reference is matched to the spectrophotometer 15 and comprises a white source (e.g., a white ceramic disc) having a color characteristic traceable to a suitable color standard, such as that established by the National Institute of Standards and Technology. Non-white (e.g., red, green, and/or blue) calibration references may also be used. During calibration, spectral data generated by the spectrophotometer 15 using the calibration reference is compared to spectral data corresponding to the calibration reference that has been previously stored within the spectrophotometer 15. Based upon this comparison, a color transform curve for suitably compensating spectral data of subsequent measurements may be generated using known methods.

For the printing device 10 of FIG. 1, automatic calibration of the spectrophotometer 15 may be problematic due to the orientation of the spectrophotometer 15 relative to the guide 20. In particular, the structure of the guide 20 generally precludes physical placement of the calibration reference at the read plane, particularly in cases where the guide 20 is a roller.

FIG. 2 illustrates an alternative placement of a calibration reference 50 as is known in the art. As shown, the calibration reference 50 is placed below a second guide aperture 55 aligned with first guide aperture 35 such that that calibration reference 50 is illuminated through the guide 20. This arrangement may not be satisfactory, however, as placement of the calibration reference 50 outside of the read plane may degrade the accuracy of the resulting spectral data, thus degrading the calibration accuracy.

FIGS. 3a-3c illustrate sequential operation of an alternative arrangement known in the art for automatically calibrating the spectrophotometer 15. In FIG. 3a, a top view of the spectrophotometer 15 and guide 20 in the normal operating position is shown. The calibration reference 50 is positioned adjacent to a side of the guide 20. During calibration, the spectrophotometer 15 is taken offline and mechanically translated such that its read plane coincides with the upper surface of the calibration reference 50, as shown in FIG. 3b. The spectrophotometer 15 is re-translated to its normal online position subsequent to calibration, as shown in FIG. 3c. Translation of the spectrophotometer 15 between the measurement and calibration positions requires the use of a full-length translation system (not shown). The internal space required for accommodating such a system may result in an unacceptable enlargement of the printing device 10.

As an alternative to the automatic calibration arrangements described above, media for which spectral data has been obtained a priori (e.g., by performing offline measurements) may be manually fed through the printing device 10. The resulting spectral data generated by the spectrophotometer 15 may then be compared to the previously-obtained spectral data in order to determine the appropriate transform curve. This calibration technique, however, is time-consuming and requires a substantial amount of manual intervention.

Because use of the spectrophotometer 15 in the measurement and calibration modes is typically intermittent, it is generally desirable to automatically store the spectrophotometer 15 within the printing device 10 during periods of nonuse such that contamination of its optical surfaces is minimized. Storage of the spectrophotometer 15 in this manner within the limited internal space of a conventional printing device is problematic and may be exceedingly difficult in cases where a large portion of the available space is allocated to spectrophotometer 15 calibration features.

In view of the problems described above, there is a need for more efficient and effective systems and methods for calibrating and maintaining electro-optical instruments within printing devices.

BRIEF DESCRIPTION OF THE FIGURES

FIG. 1 illustrates a side view of a conventional spectrophotometer arrangement within a printing device;

FIG. 2 illustrates a side view of a conventional spectrophotometer calibration arrangement within a printing device;

FIGS. 3a-3c illustrate sequential top views of a conventional spectrophotometer calibration arrangement within a printing device;

FIGS. 4a-4c illustrate sequential side views of a system for calibrating and storing a spectrophotometer within a printing device according to various embodiments of the present invention;

FIGS. 5a-5b illustrate top views of trays and arrangements of calibration references thereon for use in the system of FIGS. 4a-4c according to various embodiments of the present invention;

FIGS. 5c-5d illustrate side views of reference surfaces of the tray of FIG. 5b according to various embodiments of the present invention;

FIGS. 6a-6b illustrate sequential side views of a system for calibrating and storing a spectrophotometer within a printing device according to various embodiments of the present invention;

FIG. 6c illustrates a top view of a tray and an arrangement of a calibration reference thereon for use in the system of FIGS. 6a-6b according to various embodiments of the present invention;

FIG. 7a illustrates a side view of a system for calibrating and storing a spectrophotometer within a printing device according to various embodiments of the present invention; and, FIG. 7b illustrates a top view of a tray and an arrangement of calibration references thereon for use in the system of FIG. 7a according to various embodiments of the present invention.

DESCRIPTION

Figure 4B:
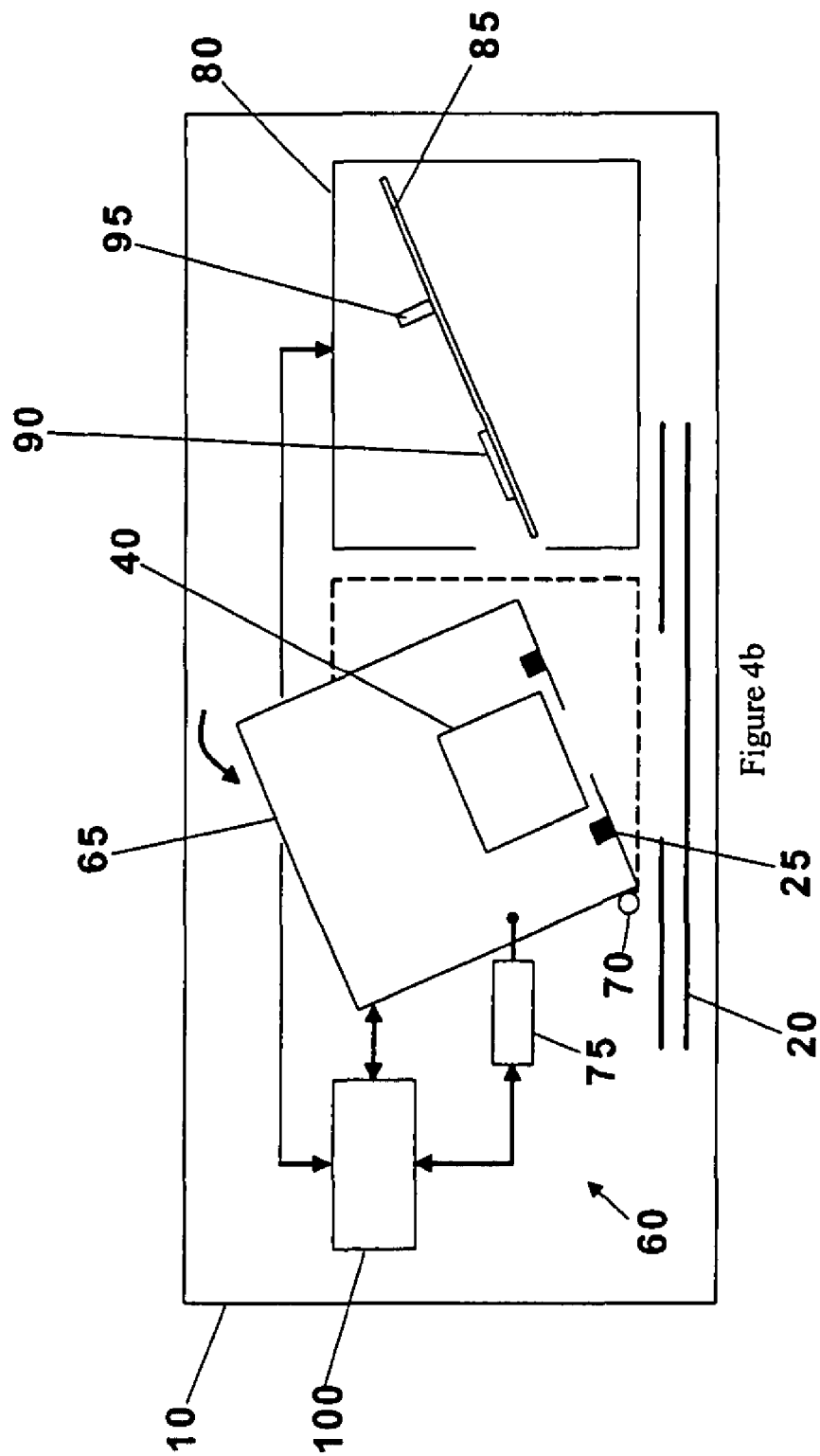

FIG. 4a illustrates a side view of a system 60 for calibrating and storing a spectrophotometer 65 within a printing device 10 according to various embodiments of the present invention. As shown, the spectrophotometer 65 comprises components similar to those described above in connection with FIG. 1 and is oriented such that its read plane corresponds to the upper surfaces of media 30 passing through the guide 20. In addition to the spectrophotometer 65, the system 60 may comprise pivot 70 attached to the spectrophotometer 65 such that spectrophotometer 65 (and its read plane) may be inclined at an angle relative to the guide 20. Although the pivot 70 is shown attached to the bottom left corner of the spectrophotometer 65, it will be appreciated that other suitable mounting locations may be employed. It will also be appreciated that the mounting location may be dictated by, among other things, the geometry, physical configuration, weight, and/or materials of the spectrophotometer 65. According to various embodiments and as shown, the pivot 70 may be implemented as a hinge, although any device or structure that enables one device to be repositioned (e.g., rotated, translated, etc.) relative to another device may generally be used.

The system 60 further comprises an actuator 75 pivotably attached to the spectrophotometer 65 for generating a mechanical force necessary to incline the spectrophotometer 65 about the pivot 70. According to various embodiments, the actuator 75 may be implemented using any suitable mechanical actuator, electromechanical actuator (e.g., a stepper motor, solenoid, etc.), hydraulic actuator, or pneumatic cylinder actuator.

The system 60 further comprises a calibration module 80 disposed adjacent to the spectrophotometer 65. As shown, the calibration module 80 comprises a calibration reference tray 85 on which one or more calibration references 90 (FIGS. 5a-5b) are arranged. As discussed below, the calibration module 80 may be configured to extend the tray 85 into the read plane of the spectrophotometer 65 when the spectrophotometer 65 is in the inclined position. The tray 85 may further include a reference surface 95 for engaging the illuminating/detecting surface of the spectrophotometer 65 when the tray 85 is extended such that the upper surface of the calibration reference(s) 90 is maintained precisely within the read plane. Other alignment features (e.g., alignment pins/sockets, etc.) may also be employed.

The system 60 further comprises a controller 100 in communication with the spectrophotometer 65, the actuator 75, and the calibration module 80. Although the controller 100 is shown separately in the embodiments of FIGS. 4a-4c, the controller 100 may be integral to the spectrophotometer 65 in other embodiments. The controller 100 may be implemented using a programmable microprocessor, for example, and in one embodiment may be configured to perform independent and fully automatic control of the system 60 responsive to one or more commands received from a printing device 10 within which the system 60 is integrated. The commands may include, for example, commands for calibrating or storing the spectrophotometer 65. In other embodiments, one or more components of the system 60 may be externally controlled by the printing device 10. The controller 100 may also read data (analog or digital) from the spectrophotometer 65, the actuator 75, and the calibration module 80. Such data may include, for example, position data (e.g., spectrophotometer 65 position data, actuator 75 position data, tray 85 position data), as well as data relating to any error conditions (e.g., position errors, mode errors, etc.). Errors may be reported by the controller 100 to a host processor (not shown) of the associated printing device 10, for example.

As shown in FIG. 4a, the spectrophotometer 65 is in a position corresponding to the measurement mode of the system 60. FIG. 4b illustrates the system 60 subsequent to initiation of the calibration or storage modes in response to a command received by the controller 100. In response to an output from the controller 100, the actuator 75 applies mechanical force to the spectrophotometer 65 such that the spectrophotometer 65 is inclined at a predetermined angle about the pivot 70.

Subsequent to the inclination of the spectrophotometer 65 and as shown in FIG. 4c, the tray 85 of the calibration module 80 is extended responsive to a controller 100 output such that a calibration reference 90 contained on the tray 85 is introduced into the read plane of the spectrophotometer 65. In various embodiments, tray 85 may be linearly extended into position using any suitable actuator (e.g., stepper motor, solenoid, etc.). According to certain embodiments, an actuator may be used to rotate/spin the tray 85 into position. Positioning of the tray 85 further results in the contact of the reference surface 95 with the illuminating/detecting face of the spectrophotometer 65 such that upper surface of the calibration reference 90 is accurately maintained within the read plane. Calibration of the spectrophotometer 65 may be automatically commenced after a properly extended tray 85 position is detected by controller 100. Subsequent to calibration, the tray 85 may be retracted and the spectrophotometer 65 declined by the actuator 75 to its normal operating position (FIG. 4a).

FIG. 5a illustrates a top view of the tray 85 and an arrangement of a calibration reference 90 thereon according to various embodiments of the present invention. Although only one calibration reference 90 is depicted, it will be appreciated that the tray 85 may instead comprise one or more additional calibration references 90 that may be positioned within the read plane by suitably controlling the linear extension of the tray 85. The tray 85 may further include a seal 105, such as, for example, a rubber seal, disposed about a periphery of the calibration reference 90. The seal 105 may be configured to contact the illuminating/detecting face of the spectrophotometer 65 such that the illumination source 25 (see, e.g., FIG. 1) and sensor module 40 optics are sealably contained and protected from external contaminants. Accordingly, the calibration position of the spectrophotometer 65 (FIG. 4c) may also correspond to its position when in the storage mode. It will be appreciated that in other embodiments, the seal 105 may be positioned on the tray 85 separately from the calibration reference 90 such that the tray 85 is positioned differently when in the calibration and storage modes.

FIG. 5b illustrates a top view of the tray 85 and an arrangement of calibration references 90 thereon according to various embodiments of the present invention. As shown, the tray 85 may be circular in shape and may comprise a plurality of calibration references 90 symmetrically disposed about a peripheral portion thereof. Subsequent to the extension of the tray 85, the calibration module 80 may be configured to rotate the tray 85 such that a selected one of the calibration references 90 is introduced into the read plane. The tray 85 may further comprise a reference surface 110 (see, e.g., FIG. 5d) for contacting the illuminating/detecting surface of the spectrophotometer 65 as the tray 85 is rotated. The calibration references 90 may include different calibration colors (e.g., white, red, green, and blue), for example. Although four calibration references 90 are shown in FIG. 5b, it will be appreciated that a different number of calibration references 90 may be used instead. The tray 85 may further include a seal 105 disposed about each calibration reference in a manner similar to that described above in connection with FIG. 5a. Accordingly, any of the calibration references 90 may be placed into the read plane to enable storage of the spectrophotometer 65 (see, e.g., FIGS. 4a-4d).

According to other embodiments, a seal 105 may be assigned to a unique position on the periphery of the tray 85 separate from that of the calibration references 90 such that no calibration reference 90 is within the read plane during storage of the spectrophotometer 65. Calibration references not located within the read plane (either during calibration or storage) can still be protected by the contact of their corresponding seals 105 with an outer-portion of the illuminating/detecting face of the spectrophotometer 65.

FIG. 5c illustrates a side view of the reference surface 110 of the tray 85 of FIG. 5b according to various embodiments of the present invention. As shown, the reference surface 110 may be contoured such that the spectrophotometer 65 is raised and lowered in accordance with the rotational position of the tray 85. This may be useful, for example, where the read plane must be adjusted to accommodate calibration references 90 of different thicknesses. Alternatively, as shown in FIG. 5d, the reference surface 110 may be uniform such that the read plane is constantly maintained.

Figure 4D:
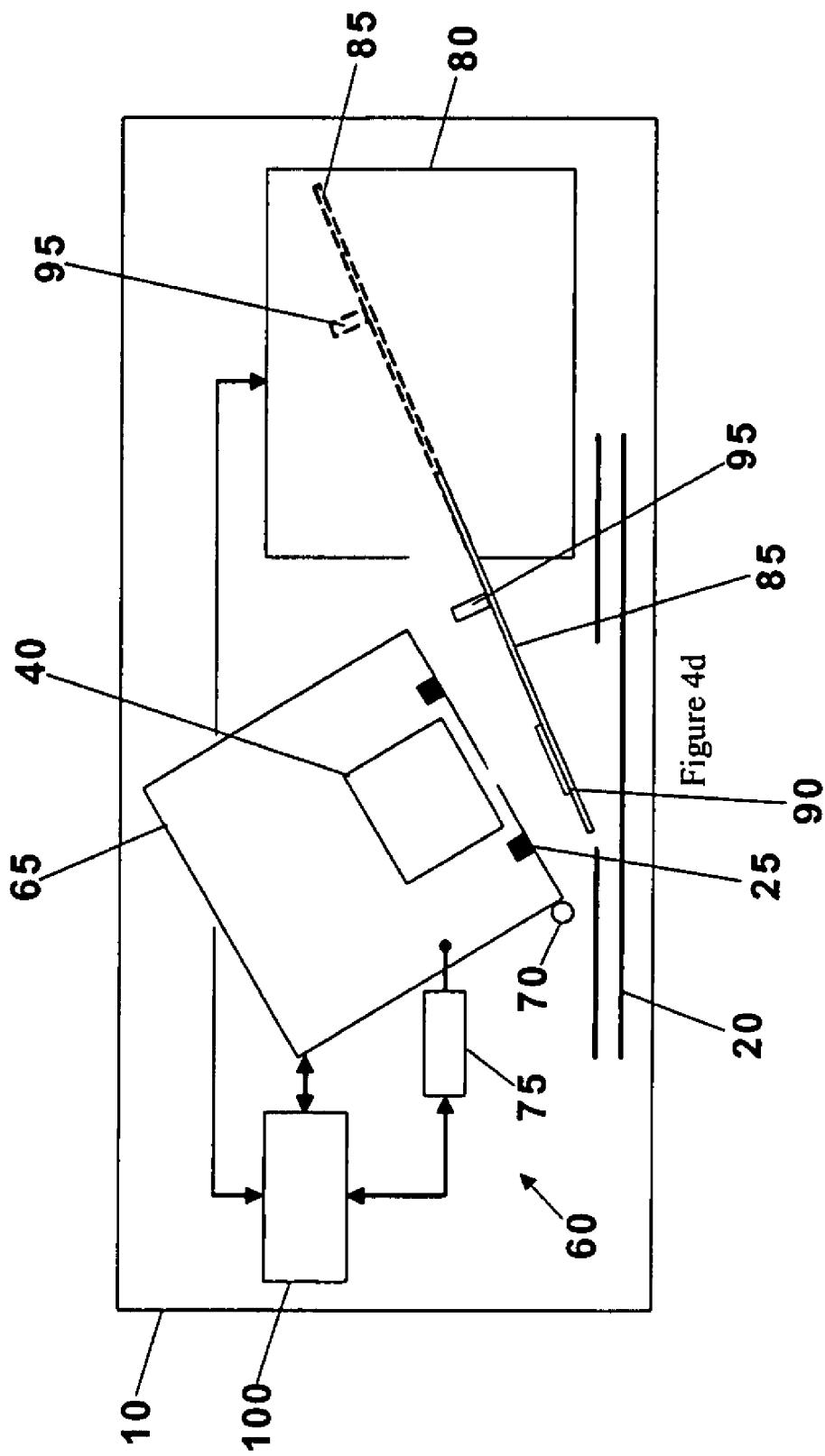
FIG. 4d illustrates a side view of the system of FIGS. 4a-4c when the spectrophotometer is inclined in a maintenance position according to various embodiments of the present invention.

In addition to the measurement, calibration, and storage positions of the spectrophotometer 65, embodiments of the present invention may further include a maintenance position whereby the inclination of the spectrophotometer 65 is increased past that corresponding to the calibration mode. FIG. 4d depicts the system 60 in which the spectrometer 60 in inclined in the maintenance position. Advantageously, the increased inclination of the spectrophotometer 60 permits the manual insertion of an external calibration reference (not shown). Additionally, the inclination may be sufficiently steep in certain embodiments such the illumination source 25 and optics of sensor module 40 may be visually inspected and/or cleaned.

Figure 6A:
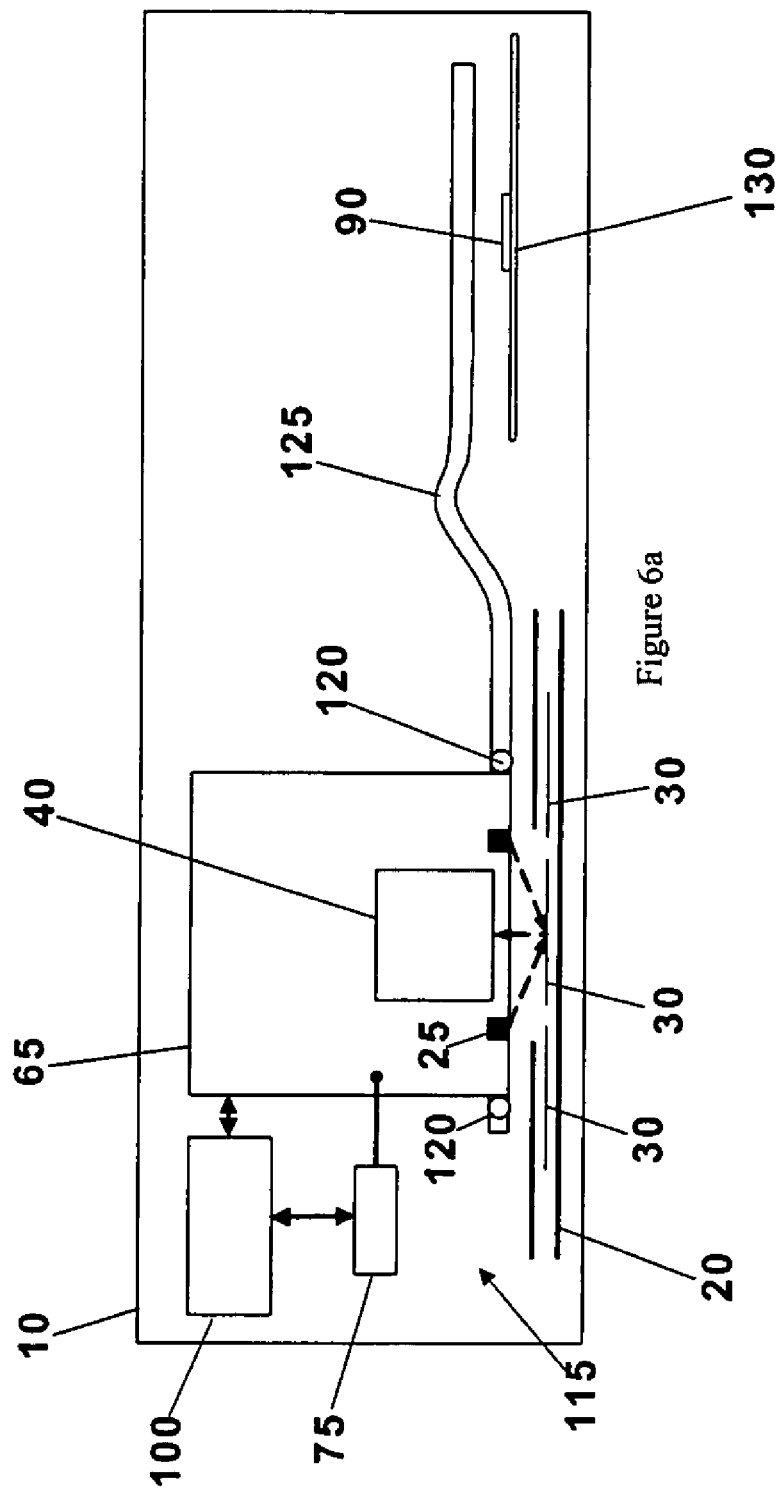

FIG. 6a illustrates a side view of a system 115 for calibrating and storing a spectrophotometer 65 within a printing device 10 according to various embodiments of the present invention. As shown, the spectrophotometer 65 can be oriented such that its read plane corresponds to the upper surfaces of media 30 passing through the guide 20. In addition to the spectrophotometer 65, the system 115 may comprise a set of guide features 120 attached to the spectrophotometer 65 and configured for receipt within a contoured cam path 125. According to various embodiments, the guide features 120 may be wheels, for example. It will be appreciated, however, that the guide features 120 may instead be implemented using non-rotating devices, such as, for example, pins. It will further be appreciated that the number and position of the guide features 120 of FIG. 6a is provided by way of example only and may be varied as needed.

The system 115 may further comprise an actuator 75 pivotably attached to the spectrophotometer 65 for generating the mechanical force necessary for causing the guide features 120 (and thus the spectrophotometer 65) to traverse the cam path 125. According to various embodiments, the actuator 75 may be implemented as an electromechanical actuator (e.g., a stepper motor, solenoid, etc.) or a pneumatic cylinder actuator, for example.

The system 115 may further comprise a tray 130 disposed adjacent to one end of the cam path 125 upon which one or more calibration references 90 (FIG. 6c) are arranged.

The system 115 further comprises a controller 100 in communication with the spectrophotometer 65 and the actuator 75. The controller 100 may be similar to that described above in connection with FIGS. 4a-4c and may be configured to respond to one or more externally-provided commands by calibrating or storing the spectrophotometer 65. The controller 100 may also read data from the spectrophotometer 65 and the actuator 75 as described above to determine their respective positions and the presence of any error conditions.

As shown in FIG. 6a, the spectrophotometer 65 is in a position corresponding to the measurement mode of the system 115. FIG. 6b illustrates the system 115 subsequent to initiation of the calibration or storage modes responsive to a command received by the controller 100. In response to an output from the controller 100, the actuator 75 applies mechanical force to the spectrophotometer 65 such that the spectrophotometer 65 traverses the cam path 125. Traversal of the cam path 125 by the spectrophotometer 65 causes the spectrophotometer 65 to be elevated above the tray 130 such that the calibration reference 90 is within the read plane. According to one embodiment, a reference surface (not shown) may be provided for engaging the transmitting/detecting face of the spectrophotometer 65 such that the calibration reference 90 is accurately maintained within the read plane. Calibration of the spectrophotometer 65 may automatically commence after the position of the calibration source 90 within the read plane is determined by the controller 100. Subsequent to calibration, the actuator 75 may cause the spectrophotometer 65 to re-traverse the cam path 125 such that it again assumes a measurement position (FIG. 6a).

FIG. 6c illustrates a top view of a tray 130 and an arrangement of a calibration reference 90 thereon according to various embodiments of the present invention. The tray 130 may be similar to the tray 85 described above and comprise a seal 105 for protecting the illumination source 25 and sensor module 40 optics from external contaminants. Accordingly, the calibration position of the spectrophotometer 65 (FIG. 6b) may also correspond to its position when in the storage mode. To protect the calibration reference 90 from contaminants, the tray 130 may further comprise a spring loaded cover (not shown) configured to extend over the calibration reference 90 when the spectrophotometer 65 is in the measurement position. The cover may be configured such that it is forcibly retracted by the spectrophotometer 65 when in the calibration position. Although only one calibration reference 90 is depicted, it will be appreciated that the tray 130 may instead comprise one or more additional calibration references 90 that may be positioned within the read plane by suitably adjusting the tray 130 position. Circular tray geometries suitable for presenting a number of calibration references 90 by rotating the tray, such as described above in connection with FIG. 5b, may also be employed.

FIG. 7a illustrates the system 115 according to another embodiment of the present invention in which the cam path 125 has been extended. According to such embodiments, multiple calibration positions may be realized by varying the position of the spectrophotometer 65 such that one of a plurality of calibration sources 90 arranged on the tray 130 (FIG. 7b) is within the read plane. According to various embodiments, one of the positions obtained by extending the cam path 125 may also be utilized to provide a maintenance mode in which the light source, optics, and other features of the spectrophotometer 65 are physically accessible for visual inspection, cleaning, and/or troubleshooting. Such troubleshooting may include, for example, manually presenting a calibration reference into the read plane.

In other embodiments, systems of the present invention may incorporate features of both systems 60, 115 described above. In certain embodiments, for example, a cam path may be provided such that traversal of the spectrophotometer 65 therethrough results in the inclination of the spectrophotometer 65 similar to that shown in FIGS. 4b-4c. A calibration module having features similar to those of the calibration module 80 may then be employed for enabling calibration or storage modes.

In still other embodiments, systems of the present invention may utilize an actuator (e.g., a screw shaft) for elevating the spectrophotometer 40 in a vertical fashion such that the read plane is maintained in a horizontal orientation. Such systems may include a calibration module similar to the calibration module 80 described above, with the exception that the tray is configured to extend horizontally into the read plane.

The examples presented herein are intended to illustrate potential and specific implementations of the present invention. It can be appreciated that the examples are intended primarily for purposes of illustration of the invention for those skilled in the art. No particular aspect or aspects of the examples is/are necessarily intended to limit the scope of the present invention.

It is to be understood that the figures and descriptions of the present invention have been simplified to illustrate elements that are relevant for a clear understanding of the present invention, while eliminating, for purposes of clarity, other elements. Those of ordinary skill in the art will recognize, however, that these and other elements may be desirable. However, because such elements are well known in the art and because they do not facilitate a better understanding of the present invention, a discussion of such elements is not provided herein.

Any element expressed herein as a means for performing a specified function is to encompass any way of performing that function including, for example, a combination of elements that perform that function. Furthermore the invention, as defined by such means-plus-function claims, resides in the fact that the functionalities provided by the various recited means are combined and brought together in a manner as defined by the appended claims. Therefore, any means that can provide such functionalities may be considered equivalents to the means shown herein.

In general, it will be apparent to one of ordinary skill in the art that various embodiments described herein may be implemented in, or in association with, many different embodiments of software, firmware, and/or hardware. The actual software code or specialized control hardware used to implement some of the present embodiments is not limiting of the present invention. For example, certain aspects of embodiments described herein may be implemented in computer software using any suitable computer software language type such as, for example, C or C++ using, for example, conventional or object-oriented techniques. Such software may be stored on any type of suitable computer-readable medium or media such as, for example, a magnetic or optical storage medium. Thus, the operation and behavior of the embodiments may be described without specific reference to the actual software code or specialized hardware components. The absence of such specific references is feasible because it is clearly understood that artisans of ordinary skill would be able to design software and control hardware to implement the embodiments of the present invention based on the description herein with only a reasonable effort and without undue experimentation.

Moreover, the processes, systems and devices associated with the present embodiments may be executed by, or in operative association with, programmable equipment, such as computers, computer systems, and spectrophotometer processor systems. Software that causes programmable equipment to execute the processes may be stored in any storage device, such as, for example, a computer system (non-volatile) memory, an optical disk, magnetic tape, or magnetic disk. Furthermore, the processes may be programmed when the computer system is manufactured or via a computer-readable medium. Such a medium may include any of the forms listed above with respect to storage devices and may further include, for example, a carrier wave modulated, or otherwise manipulated, to convey instructions that may be read, demodulated/decoded and executed by a computer.

It can also be appreciated that certain process aspects described herein may be performed using instructions stored on a computer-readable medium or media that direct a computer system to perform the process aspects. A computer-readable medium may include, for example, memory devices such as diskettes, compact discs of both read-only and read/write varieties, optical disk drives, and hard disk drives. A computer-readable medium may also include memory storage that may be physical, virtual, permanent, temporary, semi-permanent and/or semi-temporary. A computer-readable medium may further include one or more data signals transmitted on one or more carrier waves.

A "computer" or "computer system" may be, for example, a wireless or wireline variety of a microcomputer, minicomputer, server, mainframe, laptop, personal data assistant (PDA), wireless e-mail device (e.g., "BlackBerry" trade-designated devices), cellular phone, pager, processor, fax machine, scanner, or any other programmable device configured to transmit and receive data over a network. Computer systems disclosed herein may include memory for storing certain software applications used in obtaining, processing and communicating data. It can be appreciated that such memory may be internal or external to the disclosed embodiments. The memory may also include any means for storing software, including a hard disk, an optical disk, floppy disk, ROM (read only memory), RAM (random access memory), PROM (programmable ROM), EEPROM (electrically erasable PROM), and other computer-readable media.

In various embodiments of the present invention disclosed herein, a single component may be replaced by multiple components, and multiple components may be replaced by a single component, to perform a given function or functions. Except where such substitution would not be operative to practice embodiments of the present invention, such substitution is within the scope of the present invention.

While various embodiments of the invention have been described herein, it should be apparent that various modifications, alterations and adaptations to those embodiments may occur to persons skilled in the art with the attainment of some or all of the advantages of the present invention. The disclosed embodiments are therefore intended to include all such modifications, alterations and adaptations without departing from the scope and spirit of the present invention.

What is claimed is:

1. A system for positioning an electro-optical instrument within a printing device, the system comprising:
   an electro-optical instrument;
   an actuator operatively associated with the electro-optical instrument for generating a mechanical force necessary to move the electro-optical instrument along a travel path between at least: (i) a first position, wherein a read plane defined parallel to a detection face of the electro-optical instrument optically corresponds to a target region defined by a media guide of a printing device, and (ii) a second position, wherein the read plane of the electro-optical instrument has at least one of (x) a different orientation, and (y) a different elevation, relative to the first position; and
   one or more calibration references, wherein at least one of the one or more calibration references is positioned or positionable such that the read plane of the electro-optical instrument at the second position optically corresponds to a surface of the at least one calibration reference.

2. The system of claim 1, further comprising a pivot, wherein movement of the electro-optical instrument along the travel path includes rotating the electro-optical instrument about the pivot.

3. The system of claim 2, wherein the pivot includes a hinge.

4. The system of claim 1, further comprising a calibration module disposed adjacent to the electro-optical device, the calibration module including a calibration reference tray having the at least one calibration reference arranged thereon.

5. The system of claim 4, wherein the calibration module is configured to extend the calibration reference tray into the read plane of the electro-optical instrument when the electro-optical instrument is in the second position.

6. The system of claim 5, further comprising multiple calibration references arranged on the calibration reference tray such that one or more of the multiple calibration references are positionable within the read plane of the electro-optical instrument in association with extension of the calibration reference tray.

7. The system of claim 5, wherein the calibration reference tray further comprises a reference surface for engaging an illuminating or detecting surface of the electro-optical instrument when the calibration reference tray is extended into the read plane of the electro-optical instrument to maintain the calibration reference within the read plane of the electro-optical instrument.

8. The system of claim 7, wherein the reference surface of the calibration reference tray is contoured.

9. The system of claim 7, wherein the reference surface of the calibration reference tray is uniform.

10. The system, of claim 5, wherein the calibration reference tray further comprises a seal disposed about a periphery of at least one of the calibration references, the seal being structured to contact at least a portion of an illuminating or detecting face of the electro-optical instrument in the extended position of the calibration reference tray.

11. The system of claim 4, further comprising a second actuator for rotating the calibration reference tray.

12. The system of claim 4, wherein the calibration reference tray is generally circular in shape and includes a plurality of calibration references arranged thereon symmetrically disposed on the tray.

13. The system of claim 12, wherein the calibration module is configured to rotate the calibration reference tray such that a selected one of the plurality of calibration references is introduced into the read plane of the electro-optical instrument.

14. The system of claim 4, wherein the calibration module is configured to rotate the calibration reference tray such that a selected one of the at least one calibration reference is introduced into the read plane of the electro-optical instrument.

15. The system of claim 4, further comprising a controller in communication with one or more of the electro-optical instrument, the actuator, or the calibration module, the controller being configured to be responsive to one or more commands received from the printing device.

16. The system of claim 15, wherein the commands include a command selected from the group consisting of calibrating the electro-optical instrument and storing the electro-optical instrument.

17. The system of claim 15, further comprising the controller being configured to read data from one or more of the electro-optical instrument, the actuator, or the calibration module.

18. The system of claim 17, wherein the read data include at least one of electro-optical instrument position data, actuator position data, tray position data, or error condition data.

19. The system of claim 1, wherein the electro-optical instrument includes a spectrophotometer.

20. The system of claim 1, wherein the actuator includes at least one of a mechanical actuator, an electromechanical actuator, a hydraulic actuator, or a pneumatic cylinder actuator.

21. The system of claim 1, further comprising a set of guide features attached to the electro-optical instrument for facilitating moving the electro-optical instrument along the travel path.

22. The system of claim 21, wherein the set of guide features is configured to rotate the electro-optical instrument thereby adjusting the orientation of the read plane.

23. The system of claim 1, wherein the travel path is configured to adjust the elevation of the read plane of the electro-optical instrument.

24. The system of claim 1, further comprising multiple calibration references positioned adjacent to the travel path such that the read plane of the electro-optical instrument is positionable in correspondence with one or more of the multiple calibration references.

25. The system of claim 1, wherein the travel path is configured to adjust the orientation of the read plane of the electro-optical instrument.

26. The system of claim 25, wherein the adjusting the orientation of the read plane includes inclining the read plane at an angle relative to the target region defined by the media guide at the second position.

27. The method of claim 1, wherein the moving the electro-optical instrument along the travel path includes moving the electro-optical instrument along a cam path.

28. A method for calibrating an electro-optical instrument within a printing device, the method comprising:
  generating a mechanical force necessary to move the electro-optical instrument along a travel path so as to adjust at least one of (i) the orientation, and (ii) the elevation of a read plane of the electro-optical instrument relative to a media guide of a printing device;
  extending a calibration reference tray into the adjusted read plane of the electro-optical instrument, the calibration reference tray having one or more calibration references arranged thereon; and
  calibrating the electro-optical instrument with at least one of the one or more calibration references.

29. The method of claim 28, further comprising rotating the calibration reference tray after extending the calibration reference tray into the adjusted read plane of the electro-optical instrument.

30. The method of claim 29, further comprising rotating the calibration reference tray such that a selected one of the one or more calibration references is introduced into the reading plane of the electro-optical instrument.

31. The method of claim 28, wherein the moving the electro-optical instrument along the travel path includes rotating the electro-optical instrument about a pivot.

32. The method of claim 28, wherein the moving the electro-optical instrument along the travel path includes moving the electro-optical instrument along a cam path.

33. A method for calibrating an electro-optical instrument within a printing device, the method comprising:
  moving an electro-optical instrument along a travel path between at least: (i) a first position, wherein a read plane defined parallel to a detection face of the electro-optical instrument optically corresponds to a target region defined by a media guide of a printing device, and (ii) a second position, wherein the read plane of the electro-optical instrument has at least one of (x) a different orientation, and (y) a different elevation relative to the first position; and
  calibrating the electro-optical instrument with one or more calibration references, wherein at least one of the one or more calibration references is positioned or positionable such that the read plane of the electro-optical instrument at the second position optically corresponds to a surface of the at least one calibration reference.

34. The method of claim 33, further comprising moving the electro-optical instrument to one or more of multiple calibration references positioned adjacent to the travel path such that the read plane of the electro-optical instrument is positioned in correspondence with each of the one or more of the multiple calibration references.

35. The method of claim 33, further comprising moving the electro-optical instrument along the travel path to a position wherein the read plane of the electro-optical instrument is in an inclined position.

36. The method of claim 33, wherein the moving the electro-optical instrument along the travel path includes rotating the electro-optical instrument about a pivot.

37. The method of claim 33, wherein the moving the electro-optical instrument along the travel path includes moving the electro-optical instrument along a cam path.

* * * * *